United States Patent [19]
Rupilius

[11] 3,931,338
[45] Jan. 6, 1976

[54] METHOD FOR PRODUCTION OF HYDROXYALKYLGLYCOL ETHERS

[75] Inventor: Wolfgang Rupilius, Hilden Rhineland, Germany

[73] Assignee: Henkel & Cie G.m.b.H., Dusseldorf, Germany

[22] Filed: Apr. 8, 1974

[21] Appl. No.: 458,752

[30] Foreign Application Priority Data
Apr. 14, 1973 Germany............................ 2318950

[52] U.S. Cl. ....... 260/615 R; 260/458 R; 260/615 B
[51] Int. Cl.² ........................................ C07C 41/02
[58] Field of Search ..................... 260/615 R, 615 B

[56] References Cited
UNITED STATES PATENTS

| | | | |
|---|---|---|---|
| 2,723,294 | 11/1955 | Benoit............................ | 260/615 B |
| 2,782,240 | 2/1957 | Hefner et al................ | 260/615 B X |
| 2,807,651 | 6/1957 | Britton et al................... | 260/615 B |
| 3,240,819 | 3/1966 | Gaertner et al................ | 260/615 B |
| 3,242,200 | 3/1966 | Johnson ......................... | 260/615 B |
| 3,607,778 | 9/1971 | Lincoln ................... | 260/615 B UX |

FOREIGN PATENTS OR APPLICATIONS

| | | | |
|---|---|---|---|
| 1,150,345 | 4/1969 | United Kingdom ............ | 260/615 B |
| 1,193,924 | 5/1967 | United Kingdom ............ | 260/615 B |

*Primary Examiner*—Howard T. Mars
*Attorney, Agent, or Firm*—Hammond & Littell

[57] ABSTRACT

A method for the production of hydroxyalkyl glycol ethers comprises reacting non-terminal epoxides with ethylene glycol in the presence of an alkoxylation catalyst and saturated hydrocarbons, in particular, saturated aliphatic hydrocarbons, as solvents.

7 Claims, No Drawings

METHOD FOR PRODUCTION OF HYDROXYALKYLGLYCOL ETHERS

THE PRIOR ART

The reaction of non-terminal epoxides with ethylene glycol in the presence of a borontrifluoride-etherate catalyst is known. The reaction is expressed by the following equation:

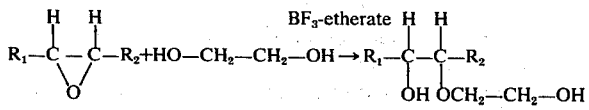

This known process has been found to be unsatisfactory in several respects. Thus, besides the formation of the desired hydroxyalkyl ether, undesirable by products are also found, whose formation may be expressed by the following reaction:

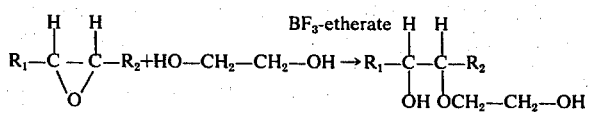

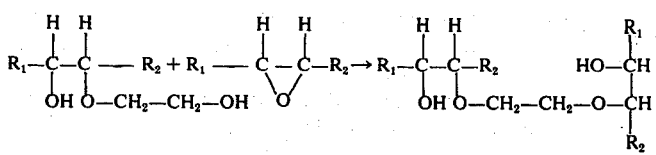

Due to this side reaction, the yield of the desired hydroxyalkylglycol ether product may be considerably reduced. Moreover the recovery of the reaction product is quite expensive, since the hydroxyalkylglycol ether product formed is contaminated by major amounts of ethylene glycol. Also the recovery, recycle and reuse of the catalyst partly involves considerable difficulties.

It has been tried in the past to suppress the formation of the by-products by conducting the reaction in the presence of excess ethylene glycol. However a satisfactory solution to the overall problem was not attained thereby; and it was still necessary to find a useful process for the production of hydroxyalkylglycol ethers from longer-chain epoxides.

OBJECTS OF THE INVENTION

It is an object of the present invention to provide a method for the production of hydroxyalkyl glycol ethers by reaction of non-terminal epoxides with ethylene glycol in the presence of an alkoxylation catalyst and saturated hydrocarbons, in particular, saturated aliphatic hydrocarbons, as solvents.

It is another object of the present invention to provide an improvement in the method for the production of hydroxyalkylglycol ethers of the formula

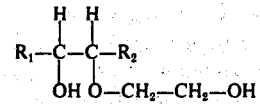

wherein $R_1$ and $R_2$ are each alkyl having 2 to 22 carbon atoms, with the proviso that the sum of $R_1$ plus $R_2$ is from 6 to 26 carbon atoms, comprising reacting a vicinal non-terminal epoxide of the formula

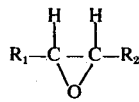

wherein $R_1$ and $R_2$ have the above-defined meanings with ethylene glycol in the presence of a catalytic amount of an alkoxylation catalyst; wherein the improvement comprises conducting said reaction in the presence of a solvent consisting essentially of a saturated hydrocarbon having 4 to 24 carbon atoms.

These and other objects of the present invention will become apparent as the description thereof proceeds.

DESCRIPTION OF THE INVENTION

The present invention concerns an improved method for the production of hydroxyalkyl glycol ethers by reaction of non-terminal epoxides with ethylene glycol in the presence of an alkoxylation catalyst and saturated hydrocarbons, in particular, saturated aliphatic hydrocarbons, as solvents.

Generally speaking it has now been found that the difficulties in the production of hydroxyalkylglycol ethers by reaction of non-terminal epoxides with ethylene glycol in the presence of alkoxylation catalysts can be largely eliminated by reacting non-terminal epoxides of the formula

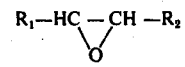

in which $R_1$ and $R_2$ are each alkyl having 2 to 22 carbon atoms with the sum of $R_1$ plus $R_2$ ranging from 6 to 26 carbon atoms, in the presence of a saturated hydrocarbon having 4 to 24 carbon atoms, in particular a saturated aliphatic hydrocarbon, as solvent, to form hydroxyalkylglycol ethers of the formula

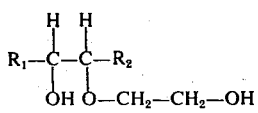

in which $R_1$ and $R_2$, as well as the sum of $R_1$ plus $R_2$ have the above defined meaning.

More particularly the present invention is directed to an improvement in the method for the production of hydroxyalkylglycol ethers of the formula

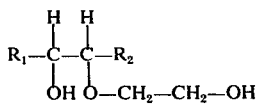

wherein $R_1$ and $R_2$ are each alkyl having 2 to 22 carbon atoms, with the proviso that the sum of $R_1$ plus $R_2$ is from 6 to 12 carbon atoms, comprising reacting a vicinal non-terminal epoxide of the formula

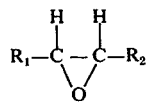

wherein $R_1$ and $R_2$ have the above-defined meanings with ethylene glycol preferably in excess, in the presence of a catalytic amount of an alkoxylation catalyst; wherein the improvement comprises conducting said reaction in the presence of a solvent consisting essentially of a saturated hydrocarbon having 4 to 24 carbon atoms.

The non-terminal epoxides serving as starting material are vicinal epoxides which can be produced by generally known methods of epoxidation of olefins with a non-terminal double bond with percarboxylic acids, hydroperoxides or oxygen in the presence of heavy metal catalysts. If the olefins to be used for the production of the epoxides are obtained, for example, by dehydrochlorination of chloroparaffins, the olefins are produced with the double bond being distributed statistically over the chain.

The vicinal non-terminal epoxides according to the invention have from 8 to 28 carbon atoms, preferably having from 10 to 14 carbon atoms, with 12 carbon atoms especially preferable. Examples of non-terminal epoxides that may be used are 3,4-epoxy-octane, 2,3-epoxy-decane, 3,4-epoxy-dodecane, 6,7-epoxy-dodecane, 4,5-epoxy-tetradecane, 2,3-epoxy-pentadecane 6,7-epoxy-octadecane, 8,9-epoxy-eicosane, 10,11-epoxy-tetracosane, 2,3-epoxy-octacosane and mixtures thereof as well as mixtures of isomers of these compounds having the epoxy-configuration distributed statistically along the chain.

Examples of alkoxylation catalysts that may be used are the acid catalysts known for the alkoxylation of substances having alcoholic hydroxyl groups, such as Lewis acids, boron trifluoride adducts, tertiary oxonium salts and compounds with stable carbonium ions. An example of such boron trifluoride adduct alkoxylation catalysts is boron trifluoride etherate.

The tertiary oxonium salts are compounds derived from aliphatic or cyclic ethers and compounds containing carbonyl groups of the formulas

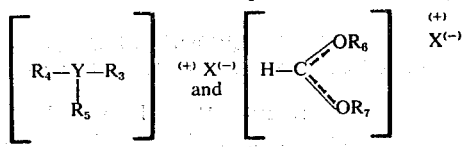

wherein
Y represents an oxygen atom or a C=O group;
X represents an unpolarizable or only slightly polarizable halogeno-complex anion, for example, $ClO_4^-$, $BF_4^-$, $FeCl_4^-$ $AlCl_4^-$, $SbCl_6^-$. $SnCl_6^{2-}$;
$R_3$ represents a lower aliphatic radical having from 1 to 4 carbon atoms, or phenyl;
$R_4$ and $R_5$ are alkyl radicals containing from 1 to 24 carbon atoms, aromatic, alicyclic or heterocyclic ring systems having from 3 to 14 ring atoms;
$R_4$ and $R_5$ can also be combined into one ring having from 4 to 14 ring atoms;
$R_6$ and $R_7$ are alkyl radicals containing from 1 to 24 carbon atoms, aromatic, alicyclic or heterocyclic ring systems having from 5 to 20 ring atoms.

The alkyl radicals described can be saturated or unsaturated, straight or branched, substituted, interrupted by hetero atoms, for example, halogen, ether groups or by cyclic groups, or bonded on Y through hetero atoms. The alicyclic or heterocyclic ring systems can be saturated or unsaturated. In the case that $R_4$ and $R_5$ are combined into one ring, this ring can, if so desired, contain hetero atoms and it can also be saturated or unsaturated. All of the ring systems mentioned can contain substituents.

Among the preferred tertiary oxonium salts are compounds of the formula selected from the group consisting of

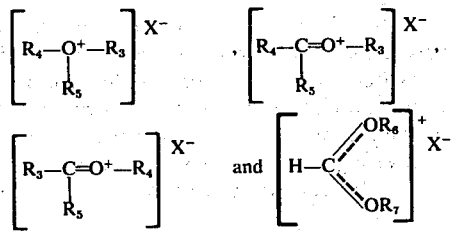

wherein
X represents a halogen complex anion selected from the group consisting of $BF_4^-$, $FeCl_4^-$, $AlCl_4^-$, $ClO_4^-$, $SbCl_6^-$ and $SnCl_6^=$;
$R_3$ represents a member selected from the group consisting of alkyl having from 1 to 4 carbon atoms, alkoxy having from 1 to 4 carbon atoms, haloalkyl having from 1 to 4 carbon atoms and phenyl;
$R_4$ and $R_5$ are members selected from the group consisting of alkyl having 1 to 24 carbon atoms, alkoxy having 1 to 4 carbon atoms, haloalkyl having 1 to 4 carbon atoms, phenyl, phenylvinyl and, when taken together, alkylene having 3 to 14 carbon atoms, oxaalkylene having 2 to 13 carbon atoms, thiaalkylene having 2 to 13 carbon atoms, azaalkylene having 2 to 13 carbon atoms, alkenylene having 3 to 14 carbon atoms, alkadienylene having 4 to 14 carbon atoms and benzobutadienylene;
$R_6$ and $R_7$ are members selected from the group consisting of alkyl having 1 to 24 carbon atoms, haloalkyl having 1 to 8 carbon atoms, phenylalkyl having from 7 to 10 carbon atoms, alkoxyalkyl having from 2 to 24 carbon atoms and cycloalkylalkyl having from 6 to 10 carbon atoms.

Among the tertiary oxonium salts used in the process of the invention, the following can be mentioned as examples:

trimethyloxonium fluoborate,
triethyloxonium fluoborate,
triethyloxonium hexachloroantimonate,
1-ethyl-1-oxa-cyclopentanium hexachloroantimonate,
tributyloxonium hexachloroantimonate,
1-(4-chlorobutyl)-1-oxa-cyclopentanium hexachloroantimonate,
trimethyloxonium tetrachloroferrate,
trimethyloxonium tetrachloroaluminate,
triethyloxonium tetrachloroaluminate,
bis-(trimethyloxonium)-hexachlorostannate,
triphenyloxonium fluoborate,
0-ethylcamphoroxonium fluoborate,
2-ethoxy-1-oxa-cyclopent-1-enium fluoborate,
0-ethyldibenzalacetonium tetrachloroaluminate,
triethylcarbonate-acidium fluoborate,
0-ethyldimethyldormimidium fluoborate,
2-ethoxy-1-thiacyclopent-1-enium fluoborate,
1-methyl-2-ethoxy-1-aza-cyclopent-1-enium fluoborate,
2,3-benzo-6-ethoxypyrylium fluoborate,
2-methyl-1,3-dioxolenium fluoborate,
2-phenyl-1,3-dioxolenium hexachloroantimonate, and
2-ethoxy-1-oxa-cyclotridec-1-enium fluoborate.

Of particular advantage is the employment of tertiary oxonium salts wherein Y of the above formula represents the C=O group, and wherein $R_3$, $R_4$, $R_5$ and X have the previous meaning, for example:

0-ethylcamphoroxonium fluoborate
2-ethoxy-1-oxa-cyclopent-1-enium fluoborate
0-ethyl-dibenzalacetonium tetrachloroaluminate and the like.

In addition, compounds of the formula

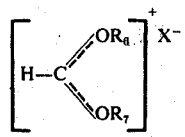

wherein $R_6$ and $R_7$ are alkyl residues containing 1 to 5 carbon atoms are particularly advantageous oxyalkylation catalysts, for example, dimethoxycarbonium tetrafluoroborate, diethoxycarbonium tetrafluoroborate, methoxyethoxycarbonium tetrafluoroborate, dibutoxycarbonium hexachloroantimonate, di-isopentyloxycarbonium hexachloroantimonate. (The nomenclature used does not describe the oxonium character of the compounds evident from the above formula, but is customary in the literature [see "Angewandte Chemie", 1966, 78, p. 714]. For a description of the oxonium structure, the catalysts might be called "dialkyl-formate-acidium salts" according to the suggestion in Houben-Weyl "Methoden der Organischen Chemie", Vol. 6/3, p. 330.)

Further examples of compounds with stable carbonium ions include those in which the carbonium salts contain as a counter-anion, particularly anions which are slightly polarizable or nonpolarizable, such as $ClO_4^-$, $BF_4^-$, $AlCl_4^-$, $FeCl_4^-$, $SbCl_6^-$, $SnCl_6^{2-}$. The carbonium ion can, for example, be triphenyl methyl, tris-p-biphenylyl-methyl, 1,4-bis-(diphenylmethyl)-benzene, diphenylmethyl-, benzyl-, xanthhydryl, diphenylpolyenyls, phenalenyl, cycloheptatrienyl (tropylium), benzotropylium, ditropylium, azulenium, heptalenium, triphenylcyclopropenylium, pentaphenylcyclopentadienyl, cyclopentenyl, heptamethylcyclohexadienyl, pentachlor-alkyl, or tricyclopropylmethyl.

The preparation of the tertiary oxonium salts can be carried out according to methods known from the literature (see Houben-Weyl, "Methoden der Organischen Chemie", Vol. 6/3, 4th Edition).

Saturated tertiary oxonium salts, wherein Y of the above formula represents an oxygen atom, are obtained, for example, by the action of metallic and non-metallic halide etherates on epoxides; by the addition of alkyl halides to metallic and non-metallic halide etherates; by alkylation of ethers with halogen alkyls and silver tetrafluoborate, as well as by the effect of aliphatic diazo compounds on primary and secondary oxonium salts. The unsaturated tertiary oxonium salts, wherein Y of the above formula represents a C=O group, are essentially prepared by alkylation of carbonyl compounds with trialkyl oxonium salts or alkyl halide/silver tetrafluoborate mixtures and by action of borontrifluoride or antimony pentachloride on acetals and ortho acid esters. The tertiary oxonium salts designated as carbonium salts are essentially prepared by reacting corresponding orthoformic acid esters with metallic and non-metallic halides which are capable of forming non-polarizable or only slightly polarizable halogen complex anions, for example, $BF_3$, $AlCl_3$, $FeCl_3$, $SbCl_5$ or $SnCl_4$.

The catalysts utilized according to the process of the invention may be utilized singly or in admixture with each other. They are usually added to the reaction mixture containing the epoxy compound in amounts of 0.05 to 5%, preferably of 0.1 to 1.5% by weight, based on the amount of the epoxy compound used.

The saturated hydrocarbons to be used as solvent according to the invention may be aliphatic hydrocarbons having 4 to 24 carbon atoms as well as a cycloaliphatic hydrocarbons having from 4 to 24 carbon atoms. Preferred are the aliphatic hydrocarbons having 4 to 24 carbon atoms, and especially preferred are those having 5 to 16 carbon atoms. Because of the relative ease in distilling, preference is given to the lower boiling point solvents. Examples of suitable solvents include cycloaliphatics, such as cycloalkane having 4 to 24 carbon atoms, preferably cycloalkane having 5 to 16 carbon atoms, for example, cyclohexane, cyclopentane and/or decahydronaphthalene; and aliphatics such as alkane having 4 to 24 carbon atoms, preferably alkane having 5 to 16 carbon atoms which may be straight-chain as well as branched-chain, for example, pentane, hexane, heptane, octane, nonane, decane, undecane, dodecane, tridecane, pentadecane and hexadecane as well as mixture thereof. Preferred for the solvent is alkane having 5 to 8 carbon atoms, such as pentane, hexane, heptane, octane and the mixtures thereof, especially preferred is pentane.

This use of saturated, in particular aliphatic hydrocarbons, as solvents in the method according to the invention for the production of hydroxyalkylglycol ethers from non-terminal vicinal epoxides offers various advantages. The yields of hydroxyalkylgylcol ethers is much higher than when operating without solvent, as the formation of by-products is greatly suppressed. The recovery of the reaction products is simplified to a substantial degree, since two layers, or phases, of essentially homogeneous composition are formed when operating by the method according to the invention. The upper layer consists of the hydroxyalkylglycol ether and the saturated hydrocarbon serving as solvent along with small quantities of ethylene glycol and by-products, while the lower phase is composed of the ethylene glycol and the catalyst dissolved therein. This greatly facilitates the recovery, recycle and reuse of the catalyst, as the latter is dissolved in the ethylene glycol phase without secondary impurities and hence can be used again and again. The reaction product obtained from the upper phase after distillation of the solvent can be used directly without further separation for various industrial applications due to the small percentage of by-products, but on the other hand, purification by distillation is possible without difficulties. In view of their low boiling points and the easy distilling connected therewith, the hydrocarbons, pentane, hexane, heptane and octane as well as their mixtures, prove particularly suitable.

For a starting material of epoxide paraffin hydrocarbon mixtures, as they are necessarily formed, for example, upon epoxidation of dehydration or dehydrochlorination olefins, the paraffin hydrocarbon may serve as solvent if it fulfills the conditions for the method of the invention. After reaction of the epoxide with ethylene glycol and separation of the ethyleneglycol-catalyst phase, the paraffin hydrocarbon can easily be separated from the formed hydroxyalkylglycol ether by distillation. Thereby a separation of the original olefin paraffin hydrocarbon mixture has been carried out simultaneously with the production of the hydroxyalkylglycol ethers.

The hydroxyalkylglycol ethers produced by the method of the invention can be further processed using known methods, for example, ethoxylation, propoxylation, sulfation, and if so desired by sulfation of the intermediate products obtained by ethoxylation or propoxylation, to form high-grade surface-active compounds. The surface-active compounds obtained in this manner can be utilized in a variety of fields of application such as manufacture of cleaning agents, cosmetics, metal treatment and metal cleaning.

The following examples are merely illustrative of the present invention without being deemed limitative in any manner thereof.

EXAMPLE 1

92 gm (0.5 mol) of epoxy-dodecane having a statistically distributed epoxy group were added dropwise during the course of half an hour at 40°C into a mixture of 155 gm of ethylene glycol (2.5 mol), 2 ml of boron trifluoride etherate, and 300 gm of pentane and the reaction mixture was then stirred for 6 hours at the same temperature. Thereafter, the two layers obtained were separated in a separating funnel with the upper layer being worked up by distillation. The results are reported in Table I.

EXAMPLE 2

155 gm of ethylene glycol (2.5 mol), 92 gm of epoxy-dodecane (0.5 mol) and 400 gm of tetradecane were charged, and then 2 ml of boron trifluoride etherate were added. The reaction and working up of the reaction mixture was carried out using a procedure analogous to that described in Example 1 and produced the results reported in Table I.

EXAMPLE 3 (COMPARATIVE)

Example 2 was repeated except that the solvent was omitted. The results are reported in Table I. Table I. Reaction of epoxy-dodecane having statistically distributed epoxide groups with ethylene glycol

| Example No. | Yield of hydroxyalkylglycol ether in gm | % of theory | Gm of by-products in the hydroxyalkylglycol ether layer | Gm of ethylene glycol in the hydroxyalkylglycol layer |
|---|---|---|---|---|
| 1 (Invention) | 110.5 | 90* | 8 | 18 |
| 2 (Invention) | 106 | 86* | 8 | 14 |
| 3 (Comparative) | 87 | 71* | 22 | 64 |

*based upon the epoxy-dodecane used.

The results of Table I indicate that the yield of hydroxyalkylglycol ether in Example 1 (The Invention) is 90/71 times the yield in Example 3 (Comparative) and that the yield in Example 2 (The Invention) is 86/71 times the yield in Example 3 (Comparative). The by-product in the hydroxyalkylglycol ether layer in Examples 1 and 2 (The Invention) were 8 gm in each case, while in Example 3 (Comparative) the by-products were 22 gm, or 2.75 times the amount according to the invention. The ethylene glycol in the hydroxyalkylglycol ether layer in Example 1 was 18 gm and in Example 2 was 14 gm, for an average of 16 gm, while the amount of ethylene glycol in Example 3 was 64 gm or 4 times the average amount according to the invention.

EXAMPLES 4 TO 8

Example 4 was carried out analogously to Example 1. The mixture of ethyleneglycol and boron trifluoride etherate obtained in this experiment and separated as the lower layer, was recycled and used again as the catalyst phase in the next example. Analogously in each of Examples 5 to 8, the mixture of ethylene glycol and boron trifluoride etherate of the respective preceding experiment was used as catalyst. The reaction was carried out in each example for 6 hours at 40°C. The results of Example 4 to 8 are reported in Table II. TABLE II. Reaction of epoxy-dodecane having statistically distributed epoxide groups with ethylene glycol in the presence of pentane as solvent with recycling of the ethyleneglycol boron trifluoride etherate layer as catalyst.

| Example No. | Yield of hydroxyalkylglycol ether in gm | % of theory | Gm of by-products in the hydroxyalkylglycol ether layer | Gm of ethylene glycol in the hydroxyalkylglycol layer |
|---|---|---|---|---|
| 4 | 108 | 88* | 10 | 15 |
| 5 | 106 | 86* | 9 | 25 |
| 6 | 114 | 93* | 8 | 22 |
| 7 | 104.5 | 85* | 9 | 19 |
| 8 | 108 | 88* | 14 | 16 |

*based upon the epoxy-dodecane used.

No further experiments with the same catalyst layer were carried out, even though no loss of activity in the catalyst was observed after the five consecutive reaction runs made as can be seen from the high yields of desired product and low amounts of by-product.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. In the method for the production of hydroxyalkylglycol ethers of the formula

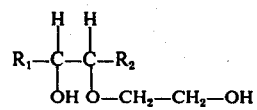

wherein $R_1$ and $R_2$ are each alkyl having 2 to 22 carbon atoms, with the proviso that the sum of $R_1$ plus $R_2$ is from 6 to 26 carbon atoms, comprising reacting a vicinal non-terminal epoxide of the formula

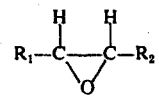

wherein $R_1$ and $R_2$ have the above-defined meanings with ethylene glycol in the presence of a catalytic amount of an acid alkoxylation catalyst; wherein the improvement comprises conducting said reaction in the presence of at least one solvent consisting essentially of at least one saturated hydrocarbon having 4 to 24 carbon atoms.

2. The method of claim 1, in which said solvent is selected from the group consisting of alkane having 4 to 24 carbon atoms and mixtures thereof and cycloalkane having 4 to 24 carbon atoms and mixtures thereof.

3. The method of claim 1, in which said solvent is selected from the group consisting of alkane having 5 to 16 carbon atoms, and mixtures thereof and cycloalkane having 5 to 16 carbon atoms and mixtures thereof.

4. The method of claim 1, in which said solvent is selected from the group consisting of cyclohexane, cyclopentane, decahydronaphthalene and mixtures thereof and pentane, hexane, heptane, octane, nonane, decane, undecane, dodecane, tridecane, pentadecane, hexadecane, and mixtures thereof.

5. The method of claim 1, in which said solvent is selected from the group consisting of pentane, hexane, heptane, octane and the mixtures thereof.

6. The method of claim 1, in which said solvent is alkane having 5 to 8 carbon atoms.

7. The method of claim 1, in which said solvent is pentane.

* * * * *

UNITED STATES PATENT OFFICE
CERTIFICATE OF CORRECTION

Patent No. 3,931,338      Dated January 6, 1976

Inventor(s) Wolfgang Rupilius

It is certified that error appears in the above-identified patent and that said Letters Patent are hereby corrected as shown below:

Item [73] Assignee: Henkel & Cie., GmbH, Dusseldorf-
Holthausen, Germany, (and)
Deutsche Gold- und Silber-Scheideanstalt
vormals Roessler (D.E.G.U.S.S.A.), Germany Signed and Sealed this Twenty-eighth Day of December 1976

[SEAL]

Attest:

RUTH C. MASON
*Attesting Officer*

C. MARSHALL DANN
*Commissioner of Patents and Trademarks*